United States Patent [19]

Pollak et al.

[11] Patent Number: 5,789,555
[45] Date of Patent: Aug. 4, 1998

[54] IMMOBILIZED LABELLING METHOD

[75] Inventors: Alfred Pollak, Toronto; Robert Dunn-Default, Bramalea, both of Canada

[73] Assignee: Resolution Pharmaceuticals Inc., Mississauga, Canada

[21] Appl. No.: 592,294

[22] PCT Filed: Nov. 16, 1994

[86] PCT No.: PCT/CA94/00637

§ 371 Date: Feb. 8, 1996

§ 102(e) Date: Feb. 8, 1996

[87] PCT Pub. No.: WO95/13832

PCT Pub. Date: May 26, 1995

[51] Int. Cl.⁶ .................................................. C07F 13/00
[52] U.S. Cl. .......................... 534/14; 534/10; 424/1.11; 424/1.65
[58] Field of Search .................. 424/1.11, 1.37, 424/1.53, 1.65, 9.1; 534/7, 10–16; 530/300, 324–330, 333, 334, 338

[56] References Cited

U.S. PATENT DOCUMENTS

| | | | |
|---|---|---|---|
| 4,272,503 | 6/1981 | Camin et al. | 424/1.11 |
| 4,305,922 | 12/1981 | Rhodes | 424/1.11 |
| 4,361,497 | 11/1982 | Boldt et al. | 252/426 |
| 4,659,839 | 4/1987 | Nicolotti et al. | 548/546 |
| 4,988,496 | 1/1991 | Srinivasan et al. | 424/1.11 |
| 5,059,541 | 10/1991 | Fritzberg et al. | 436/501 |
| 5,089,249 | 2/1992 | Fritzberg et al. | 424/1.11 |
| 5,162,505 | 11/1992 | Dean et al. | 530/391.5 |
| 5,206,346 | 4/1993 | Taylor | 530/391.3 |
| 5,480,970 | 1/1996 | Pollak et al. | 530/328 |
| 5,569,745 | 10/1996 | Goodbody et al. | 530/328 |

FOREIGN PATENT DOCUMENTS

| | | |
|---|---|---|
| 0324323 | 7/1989 | European Pat. Off. |
| 9216840 | 10/1992 | WIPO |

OTHER PUBLICATIONS

Bioconjugate Chemistry, vol. 1, No. 6, 1990, Washington, pp. 431–437 Weber et al. "Enhanced kidney clearance with an ester-linked . . .".

Proc Natl Acad Sci USA, Oct. 1986, vol. 83, No. 19, pp. 7187–91, Bump et al. "Isolation and subunit composition of tuftsin receptor".

WO, A, 92 11032, published Jul. 9, 1992.

J. Nucl. Med., vol. 34, No. 11, pp. 1953–63, Nov. 1993, Visser et al, "Labeling of monoclonal antibodies with rhenium–186 using the MAG3 . . .".

Cancer Res., vol. 53, No. 15, pp. 3524–9, Aug. 1993, Gerretsen, et al, "Rhenium–186–labeled monoclonal antibody E48 immunoglobulin G–mediated . . .".

J. Biochem (Tokyo, JP) vol. 108, No. 4, pp. 635–641, 1990, Suzuki et al., "Chemical Modification of Pig Liver Initiation Factor EIF–2 with N . . .".

Mol Cell Biochem, vol. 92, No. 1, pp. 77–84, 1990, Bump et al, "The Characteristics of Purified HL–60 Tuftsin Receptors".

38th Annual Meeting of the Society of Nuclear Medicine, Jun. 11–14, 1991, Sood et al, "Use of 4 pyridylsulfide as a thiol protecting group of . . .".

36th Annual Meeting of the Society of Nuclear Medicine, Jun. 13–16, 1989, Dean et al, "Ester–linker technetium–99M labeled antibody–bifunctional . . .".

37th Annual Meeting of the Society of Nuclear Medicine, Jun. 19–22, 1990, Weber et al, "Hydroylsis of an ester linked technetium–99M labeled . . .".

IXth International Symposium on RadioPharmacetical Chemistry, Apr. 6–10, 1992, Jeong et al, "Synthesis of a Technetium–99M MAG3 Biotin . . .".

*Primary Examiner*—John Kight
*Assistant Examiner*—Dameron Jones
*Attorney, Agent, or Firm*—Nikaido, Marmelstein Murray & Oram LLP

[57] ABSTRACT

Described is a process for labelling ligands with metals comprising the steps of covalently coupling the ligand to a solid support via a metal-cleavable linker; introducing a complex-forming metal to the support; and collecting the metal-ligand complex released from the support. The metal catalyzes cleavage of the ligand from the support upon complex formation resulting in a solution substantially free of unlabelled ligand.

22 Claims, 1 Drawing Sheet

IMMOBILIZED LABELLING METHOD

FIELD OF THE INVENTION

This invention relates to compositions and processes useful for generating metal-ligand complexes. In one specific respect, the invention relates to metal-labelled compounds useful as imaging agents in the field of medical diagnostics.

BACKGROUND OF THE INVENTION

The art of diagnostic imaging exploits agents that in binding or localizing site selectively within the body, help to resolve the image of diagnostic interest. Gallium citrate, for example, has an affinity for tumours and infected tissue of the body and, with the aid of scanning tomography, can reveal afflicted body regions to a physician. Magnetic Resonance Imaging (MRI) differentiates tissue types by their physicochemical properties and can therefore detect tissues altered physicochemically by disease. To enhance detection, imaging agents are employed that affect the rate of proton relaxation of water molecules in the body upon irradiation by a magnetic field. Typical MRI agents comprise a water soluble, non-toxic organic chelator complexed with a paramagnetic metal, for example gadolinium-ethylenediaminetetraacetic acid (Gd-EDTA). Other imaging agents used in diagnostic imaging incorporate targeting molecules, such as proteins, peptides and antibodies that localize at desired regions of the human body and are labelled with a radionuclide metal such as technetium and rhenium. Localization of these imaging agents is detected by gamma camera analysis.

Labelling of imaging agents with metal atoms is made difficult by their chemical structure. Conventional labelling techniques involve the formation of the metal complex in a solution of excess ligand which typically results in high levels of unlabelled ligand. For example, technetium labelling reactions yield approximately one labelled ligand for every thousand or more unlabelled ligand. For many imaging agents, there is a finite number of binding sites ie. receptors, for which both the labelled and unlabelled imaging agent compete. This necessitates administration of larger doses of the imaging agent in order to achieve an image. Presently, high performance liquid chromatography (HPLC) is applied to enhance the concentration of labelled imaging agent in the solution before it is administered. While enhancing concentration, this separation step requires additional time and expense which make it impractical for clinical use.

It is an object of the present invention to provide a composition useful for generating labelled imaging agent.

It is also an object of the present invention to provide a process for preparing compositions useful for generating labelled imaging agent that is substantially free of unlabelled imaging agent.

A further object of the present invention is to provide a method of using compositions to generate preparations of labelled imaging agent that are substantially free of unlabelled imaging agent, in particular metal-labelled compounds useful for diagnostic imaging.

SUMMARY OF THE INVENTION

According to one aspect of the invention, there is provided a composition useful for generating a metal labelled imaging agent comprising: a solid support; a linking group bound to the solid support; and a ligand incorporating at least one metal coordinating atom that is coupled to the linking group by a bond cleavable by said metal wherein said ligand is further coupled to a targeting molecule that is free of metal binding sites.

According to another aspect of the present invention, there is provided a process for generating a metal-ligand complex, comprising the steps of (1) obtaining a composition in which a metal coordinating atom of a ligand is coupled to a linking group bound to a solid support wherein the ligand is further coupled to a targeting molecule thereby forming a ligand-targeting molecule conjugate;

(2) bringing the composition into contact with said metal to cause the formation of a coordinate bond between the metal and the metal coordinating atom and thereby to cause release of a metal labelled conjugate from the support; and (3) collecting the metal labelled conjugate so released.

In a further aspect of the invention, there is provided a composition useful for generating a metal labelled imaging agent, the composition comprising: a solid support; a maleimide linking group bound to the solid support; and a ligand incorporating at least one metal coordinating sulfur atom that is coupled to the linking group by a bond cleavable by said metal.

In yet another aspect of the invention, there is provided a process for generating a metal labelled imaging agent, comprising the steps of:

(1) obtaining a composition comprising a solid support; a maleimide linking group bound to the solid support; and a ligand incorporating at least one metal coordinating sulfur atom that is coupled to the linking group by a bond cleavable by said metal;

(2) contacting the composition with said metal to cause the formation of a coordinate bond between the metal and the metal coordinating sulfur atom thereby causing the release of a metal labelled ligand from the support; and (3) collecting the metal labelled ligand so released.

DETAILED DESCRIPTION OF THE INVENTION

Figure 1:
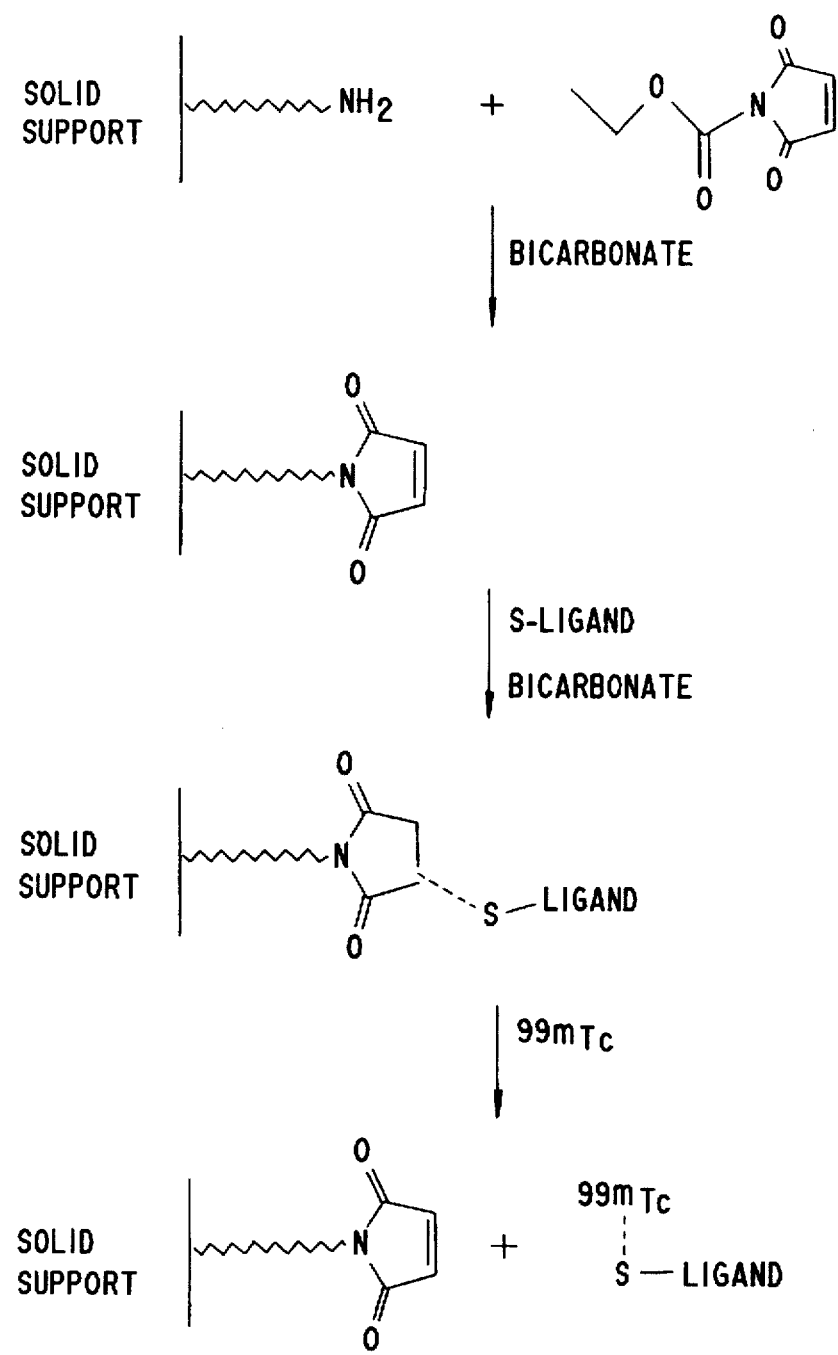
FIG. 1 is a schematic diagram illustrating loading and labelling of a ligand on a maleimide functionalized solid support.

With the present invention, the process of generating a metal-ligand complex is simplified by the strategy of coupling the ligand to a solid support through a metal-cleavable linking group. In this way, the single step of introducing a metal to the immobilized ligand results not only in the formation of metal-ligand complexes, but also in the consequential release of those complexes from the support for collection in a form substantially free of uncomplexed ligand.

According to an aspect of the present invention, compositions are provided that are useful for generating metal labelled imaging agents that are substantially free of the unlabelled imaging agent comprising: a solid support; a linking group bound to the solid support; and a ligand incorporating at least one metal coordinating atom that is coupled to the linking group by a bond cleavable by said metal wherein said ligand is further coupled to a targeting molecule that is free of metal binding sites.

According to another aspect of the present invention, compositions are provided that are useful for generating metal labelled imaging agents that are substantially free of unlabelled imaging agent. Compositions of the present invention comprise a solid support; a maleimide linking group bound to the solid support and a ligand incorporating a metal coordinating sulfur atom that is coupled to the linking group by a bond that is cleaved in the presence of a metal. The bond between the maleimide linking group and the metal coordinating atom of the ligand is cleaved upon formation of a coordination bond between the coordinating atom and the metal.

The term "ligand" refers to compounds that incorporate at least one metal coordinating atom capable of forming a coordinate bond with a given metal, thereby forming a stable metal-ligand complex. A ligand may contain one or more metal-coordinating atoms; in the case where a ligand contains two or more metal-coordinating atoms the ligand may be referred to as a "chelator". Ligands that contain two or more coordinating atoms, referred to as multidentate, typically form more stable metal-ligand complexes than do monodentate ligands and are preferred for this reason. Many ligands that bind to radionuclide metals are tetradentate containing a combination of four nitrogen and sulfur metal-coordinating atoms ie. $N_4$, $N_3S$ and $N_2S_2$, however they may incorporate other metal-coordinating atoms such as oxygen, phosphorous and selenium. For diagnostic imaging it is particularly desirable that the metal complex is highly stable in vivo so that the metal is not released from the ligand in substantial quantities and accumulate in tissues. The present invention can be applied to a wide variety of ligands, such as $N_3S$ chelators described in co-pending PCT application CA94/00395 filed on Jul. 18, 1994 and $N_2S_2$ chelators described in co-pending PCT application CA94/00479 filed on Aug. 18, 1994, however preferred ligands are peptides or derivatives thereof which incorporate a pendant sulfhydryl group for binding to a metal. Suitable peptidic chelators are those described in WO 9317719 which are amenable to coupling to targeting molecules, particularly targeting molecules that are also peptidic. In one embodiment, the invention is applied to label ligands that have intrinsic targeting properties. One such ligand available for radiodiagnostic imaging is mercapto-acetyl-glycyl-glycyl-glycine (MAG3) which localizes in renal tissue and may be labelled according to the method of the present invention to prepared renal imaging agents. MAG3 is an $N_3S$ class of ligand having three nitrogen coordinating atoms and one sulfur coordinating atom.

Targeting molecules suitable for use in compositions of the invention are compounds that are capable of localizing selectively in vivo at sites for imaging such as at a particular organ, tissue or cell type. Examples of targeting molecules include, but are not limited to, steroids, antibodies, proteins, peptides, nucleotides and saccharides. Preferred targeting molecules include proteins and peptides, particularly those capable of binding with specificity to cell surface receptors characteristic of a particular pathology. Preferably, targeting molecules are peptides or derivatives thereof comprising 3 or more amino acid residues that bind to cell surface receptors such as those described in co-pending CA94/00395 (supra). Preferably, targeting molecules are peptides comprising approximately 3 to 50 amino acids and more preferably 3 to 10 amino acids. In an embodiment, targeting molecules are chemotactic peptides that bind to cell surface receptors and in particular are chemotactic peptides that incorporate the amino acid sequence TKPPR (SEQ ID No: 1).

In the particular process aspect of the invention wherein the ligand coupled to the linking group is further coupled to a targeting molecule, it is desirable that the targeting molecule itself be free of metal binding sites such as pendant sulfhydryl groups. A ligand-targeting molecule conjugate labelled according to this particular process wherein the targeting molecule presents metal binding sites such as pendant sulfhydryl groups found in cysteine residues may 1) lose some or all of its localizing activity and 2) release metal in vivo thereby increasing background noise and obscuring the image.

Ligands and/or targeting molecules that are peptidic are commercially available or may be synthesized de novo by solid phase techniques or by recombinant DNA techniques. Solid-phase peptide synthesis generally involves the use of automated synthesizers and an appropriate support as the solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of the peptide from the support, and the peptide is then isolated. Common purification techniques include reversed-phase HPLC using acetonitrile as solvent and trifluoroacetic acid as an ion-pairing agent. Procedures are described in numerous publications. Reference may be made to Stewart and Young, *Solid Phase Peptide Synthesis*, 2nd Edition, 1984, Pierce Chemical Company, Rockford, Ill. Alternatively, peptides may be synthesized in solution or on a solid phase in small blocks and subsequently ligated to give the desired sequence. Peptides incorporating amino acids that are not genetically encoded require synthetic techniques for preparation.

The term "solid support" refers to any substrate that is insoluble and inert in labelling solutions and can be functionalized with a linking group. Suitable solid supports include inorganic silicate glass, silica or alumina beads and organic polystyrene, polyacrylamide or sugar polymers such as Sephadex. Preferred solid supports of the invention are commercially available alkylamino functionalized controlled-pore glass, agarose, acrylic and silica. The amino group serves as a reactive site for coupling linking groups to the supports. Most preferred is a long chain alkylamino controlled-pore glass support which provides for less sterically hindered coupling of linking groups. The support may be provided as a powder or a ball contained in a tube or as a coating on the inside of a vessel. For the purposes of generating metal-ligand complexes it is preferred that the support be in a column that allows for easy passage, collection and filtration of the complex solution.

The term "linking group" refers to a chemical entity that can be covalently bound to a support or to functionalized groups thereof and can form a bond with a coordinating atom of a ligand. A suitable linking group is one that is capable of immobilizing a ligand on a support in the absence of a complex-forming metal yet allows release of the ligand upon formation of a coordinate bond between the metal and the coordinating atom of the ligand. An essential feature of a linking group is that it remains bound to the support in its entirety under complex-forming reaction conditions. A linking group is selected according to the type of coordinating atom in the ligand. When the coordinating atom is sulfur, a metal-cleavable thiol protecting group may serve as a linker. Several examples of thiol protecting groups that are cleavable by metals are described in *Protective Groups in Organic Synthesis*, 2nd ed., Greene and Wuts, John Wiley & Sons, New York, 1991. For example various parasubstituted benzyl groups such as p-methoxybenzyl, p-nitrobenzyl; triphenylmethyl; t-butyl; adamantyl; dihydropyran; and maleimide may be used. A commercially available alkyl amine glass support can be functionalized with a thiol-protecting group such as a dihydropyran linking group, by reacting the support with dihydropyran carboxylic acid which binds the linking group to the support via an amide group. A selected ligand may then be coupled to the dihydropyran functionalized support by reacting the support and the ligand in the presence of dimethylformamide (DMF).

In a particular aspect, compositions of the invention comprise a solid support that is functionalized with a maleimide linking group that forms a metal cleavable bond with a metal coordinating sulfur atom of a ligand. Maleimide may be loaded to various solid supports by established chemical techniques, for example, obtaining an alkylamine functionalized form of the support and reacting with a suitable maleimide ester such as N-maleimidoethyl formate or maleimidopropionic acid N-hydroxysuccinimide ester (Sigma). To the maleimide functionalized support may then be coupled a selected ligand incorporating a pendant sulfhydryl group by reacting the support with the ligand in the presence of sodium bicarbonate.

When the coordinating atom is an amino nitrogen, suitable linking groups include metal-cleavable amino protecting groups, for example, ethyl esters such as trichloroethyl ester, trimethylsilylethyl ester and phenyl-ethyl ester; as well as vinyl ester; and allyl ester groups. These amino protecting groups bind ligands to form carbamates that are metal-cleavable. In the case where the coordinating atom is an amide nitrogen, suitable linking groups include metal-cleavable amide protecting groups such as an allyl group. A ligand containing an oxygen coordinating atom may be coupled to a linking group that is a metal-cleavable hydroxy protecting group such as methylthiomethyl and t-butylthiomethyl. Conditions and reagents for coupling and cleaving metal-cleavable protecting groups to ligands are described in Greene and Wuts (supra).

The terms "metal" or "complex-forming metal" refers to any metal atom that is in a state capable of forming stable coordination bonds with metal coordinating atoms of a ligand. Metals that are capable of forming complexes include the transition metals, lanthanide metals and actinide metals. For use in MRI, the metal can be a paramagnetic metal atom such as divalent and trivalent chromium, manganese, iron, cobalt, nickel, copper, praseodymium, neodymium, samarium, ytterbium, terbium, dysprosium, holmium, erbium and gadolinium. The more preferred metals for MRI are those exhibiting a strong magnetic moment, such as gadolinium and manganese. The halide salt, in particular chloride salt, or oxide of these metals are forms capable of complexing with a desired ligand and are suitable for the present invention. Radionuclide labelled imaging agents employ metal isotopes that include β-emitters such as rhenium-186 and -188; and γ-emitters such as technetium-99m. The metal most preferred for radiodiagnostic imaging is technetium-99m due to its advantageous half life of 6 hours and inexpensive preparation from a molybdenum-99 generator. Technetium and rhenium labelling is accomplished by procedures established in the art. Either metal may be introduced to the ligand in aqueous solution in oxo, dioxo or nitrido form, for example pertechnetate ($^{99m}TcO_4$) or perrhenate, with a suitable reducing agent such as stannous chloride. Alternatively, radiodiagnostic agents may be formed by a transchelation reaction which entails use of the metal in the form of a weak metal complex such as technetium-gluconate, heptagluconate, tartrate or citrate to give a desired labelled ligand. Transchelation reactions are typically heated to facilitate conversion of technetium from the weak complex to a complex with the ligand, for example in a boiling hot water bath.

According to a process of the present invention, ligand-targeting molecule conjugates are labelled with complex-forming metals to provide a solution substantially free from unlabelled conjugate. In general, the process comprises the steps of obtaining a composition in which the ligand of the conjugate is coupled covalently to a solid support via a metal-cleavable linking group; introducing a complex-forming metal to the support; and collecting the labelled conjugate released from the support. In this process the metal forms a coordination bond with a metal coordinating atom of the ligand coupled to the linking group thereby cleaving the covalent bond between the ligand atom and the support. As a result, only labelled conjugate is released from the support.

According to another process of the present invention, ligands are labelled with complex-forming metals to provide a solution substantially free of unlabelled ligand. As illustrated in FIG. 1, the process comprises the steps of obtaining a composition in which a maleimide linking group is coupled to a solid support and to a metal coordinating sulfur atom of a ligand. While the process of the present invention can be employed in the production of various metal complexes that incorporate coordinating sulfur atoms, a particularly useful application is the production of diagnostic imaging agents. In a particular embodiment, the process of the invention further comprises the step of coupling the metal labelled ligand with a targeting molecule to form a conjugate. Conjugates may be formed by reacting a ligand which incorporates a conjugating group with a corresponding reactive group on the targeting molecule thereby forming a stable covalent bond. For example, an ester group on the ligand may react with an amino group on the targeting molecule or visa versa to form an amide bond. When both the ligand and targeting molecule are peptides, a conjugate is most preferably formed via a peptide bond.

In a specific embodiment of the process of the present invention, a peptide mercaptoacetyl-glycyl-glycyl-glycine (MAG3) was labelled with technetium-99m to form a radiodiagnostic renal imaging agent. Glycyl-glycyl-glycine was synthesized by solid-phase synthesis and subsequently derivatized with mercaptoacetic acid to give MAG3. A solution of the peptide at pH 6.8 was then introduced by syringe to a maleimide functionalized controlled-pore glass support. After several hours the solution was filtered off and the loaded support washed with methanol and dichloromethane and then dried. The support was initially prepared by addition of maleimidopropionic acid N-hydroxysuccinimide ester in triethylamine and dimethylformamide to a commercially available long chain alkyl amine glass support. The support was filtered and washed with methanol and then dried. $^{99m}Tc$ was added to the MAG3 loaded support as pertechnetate with stannous heptagluconate and then heated to facilitate complex formation. After 10 minutes virtually all technetium had formed a complex with MAG3 which was no longer immobilized on the support.

In another specific embodiment of the process of the present invention, MAG3 was loaded onto dihydropyranyl functionalized support. The dihydropyranyl support was prepared by adding dihydropyran carboxylic acid sodium salt in dimethylformamide and 1-(3-dimethylaminopropyl)-3-ethylcarbodiimide hydrochloride (EDCI) to a long chain alkylamine glass support under vacuum. After three hours the support was filtered and washed with dichloromethane, water and ether and then dried. MAG3 was loaded onto the support by adding a solution of the peptide in DMF under argon. After several hours the support was filtered and washed with DMF and dichloromethane and then dried.

EXAMPLE 1

Preparation of S-protected Mercaptoacetyl-Gly-Gly-Gly:

To a purged stirring solution at 0° C. of (5.74 g, 41.6 mmoles) thiobenzoic acid in (100 mL) ethanol was added (27.8 mL, 3N, 83.2 mmoles) potassium hydroxide followed by (7.70 g, 41.6 mmoles) iodoacetic acid in (30 mL) ethanol. The solution stirred for 10 hours at room temperature under argon. The ethanol was rotavapped and the orange solid product was dissolved in (40 mL) water. The solution was acidified to pH 2.0 where an orange precipitate formed. This was filtered, washed with water, and dried in vacuo to give an orange-pink solid, benzoylmercaptoacetic acid (7.98 g, 99% yield).

To a stirring solution of (9.20 g, 46.9 mmoles) benzoylmercaptoacetic acid and (5.41 g, 46.9 mmoles) N-hydroxysuccinimide in (100 mL) dioxane was added a solution of (9.70 g, 47 mmoles) dicyclohexylcarbodiimide in (40 mL) dioxane. The reaction stirred 12 hours followed by cooling to 4° C., filtering, and rotavapping off the dioxane to a white solid. This was triturated with cold isopropanol, filtered, and dried in vacuo (10.8 g, 78% yield). 200 mg of benzoylmercaptoacetic N-hydroxysuccinimide was recrystallized from 500 mg in hot ethyl acetate.

To a stirring solution of (945 mg, 5 mmoles) glycylglycyl-glycine (Gly-Gly-Gly) prepared by solid-phase synthesis, and (850 mg) sodium bicarbonate in (20 mL) water was added dropwise a solution of (1.47 g, 5 mmoles) benzoylmercaptoacetic N-hydroxysuccinimide ester in (20 mL) acetone. The solution stirred at room temp. for 2 hours. The solvent was rotavapped down to 10 mL and conc. hydrochloric acid was added dropwise to form a white precipitate, N-(S-benzoylmercaptoacetyl)Gly-Gly-Gly (N-S-benzoyl-MAG3). This was filtered washed with water and dried in vacuo, (yield: 1.70 g, 92.4%).

Preparation of Dihydropyranyl Support:

To (3.0 g, 300 µmoles) of long chain alkyl amine glass support (500 Å pore diameter, 125–177µ particle size, Sigma) under vacuum was added a solution of (2.0 g, 3.3 mmoles) 1-(3-dimethylaminopropyl)-3-ethylcarbodiimide hydrochloride (EDCI), (483 mg, 3.3 mmoles) dihydropyran carboxylic acid sodium salt in (20 mL) dimethylformamide. The orange solution was shaken for three hours. The support was filtered and washed with dichloromethane and then dried in vacuo.

To check the loading of dihydropyran on the support, the following steps were performed: to (100 mg) dihydropyran loaded glass support was added a solution of (350 µL) mercaptoethanol in (1.5 mL) dichloromethane. After 2 hours the support was filtered and washed with dichloromethane until the thiol smell disappeared. (60 mg) were derivatized with (800 mg) dimethoxytrityl chloride in (2 mL, 3:1) DMF/pyridine overnight for 16 hours. The tritylated support was filtered and washed several times with dichloromethane. The dimethoxytrityl group was cleaved off 7 mg of the support in (10 mL, 3:2) perchloric acid/ethanol after 5 minutes to a dark orange colour. After dilution and UV analysis of the supernatant the dihydropyran loading was indirectly determined to be a minimum of 73.1 µmoles/g.

Loading MAG3 on Dihydropyranyl Support:

Sulfur protected MAG3 (N-S-benzoyl-MAG3) was deprotected by the following steps. To a solution of (370 mg, 1 mmole) benzoyl-MAG3 in (10 mL) water under argon was added (440 µL, 5N, 2.2 mmoles) sodium hydroxide solution. After heating the solution at 60° C. for 10 minutes the solution was acidified to pH 2 with (2N, 2.2 mmoles) hydrochloric acid. The solution was rotavapped to a pale yellow oil.

To (200 mg) dihydropyran loaded glass support under vacuum was added a solution of (1 mmole crude) MAG3 in (5.0 mL) dimethylformamide under argon. Upon addition, heat was detected. The solution was shaken for 16 hours, then filtered, washed with dimethylformamide, dichloromethane, and then dried in vacuo.

EXAMPLE 2

Preparation of Maleimide Functionalized CPG Support:

To (300 mg, 30 umoles) long alkyl chain amine loaded glass support (Sigma) under vacuum was added a solution of (100 mg, 375 umoles) maleimidopropionic acid N-hydroxysuccinimide ester (Sigma), and (100 µL) triethylamine in (5 mL) dimethylformamide. The solution was shaken for 16 hours, filtered, washed with methanol, and dried in vacuo. Ninhydrin test for amines showed negative, indicating a complete reaction.

Preparation of a maleimide functionalized support was also accomplished by the following steps. To (3.0 g) glass support under vacuum was added by syringe a solution of (558 mg, 3.3 mmoles) maleimidopropionic acid, (2.0 g, 9.9 mmoles) EDCI, and (0.1 eq, 330 µmoles) 4-dimethylaminopyridine (DMAP) in (20 mL) DMF. The solution was rotated overnight followed by filtration, washing with dichloromethane and drying in vacuo.

A most preferred method of preparing maleimide support is accomplished by the following steps. To (500 mg, 50 µmoles) long alkyl chain amine loaded glass support (Sigma) under vacuum was added a solution of (50 mg, 185 umoles) maleimidopropionic acid N-hydroxysuccinimide ester in (3 mL, 1:1) water:acetone, buffered to pH 7.5 with (10 mg) sodium bicarbonate. The solution was shaken for 2 hours where a negative ninhydrin test showed a complete reaction. The maleimide loaded support was filtered, washed with water, and dried in vacuo.

Loading MAG3 on Maleimide Support:

Method 1. To (200 mg) maleimide loaded glass support under vacuum was added a solution of (1 mmole crude) mercaptoacetyl-gly-gly-gly in (5.0 mL) dimethylformamide under argon. Upon addition heat was detected. The solution was shaken for 16 hours, then filtered, washed with dimethylformamide, dichloromethane, and then dried in vacuo.

Method 2. Alternatively MAG3 may be loaded onto maleimide support by the following steps. To a solution of (335 mg, 0.91 mmole) benzoylmercaptoacetyl-gly-gly-gly in (10 mL) water under argon was added (400 µL, 5N, 2.0 mmoles) sodium hydroxide solution. After heating the solution at 50° C. for 30 minutes the solution was acidified to pH 6.5 with (2N, 2.2 mmoles) hydrochloric acid and then to pH 6.8 with a sodium bicarbonate solution. This solution was filtered and added via syringe to (1.50 g) evacuated maleimide loaded glass support. The reaction rotated for several hours before washing with methanol on a filter frit, then dichloromethane, filtering, and drying in vacuo. Amino acid analysis showed a loading of 7.3 µmoles/g.

Method 3. Preferably MAG3 is loaded onto maleimide support by the following steps. To a solution of (110 mg) benzoylmercaptoacetyl-Gly-Gly-Gly in (4 mL) water under argon was added (5N) sodium hydroxide solution. After heating the solution at 50° C. for 10 minutes the solution was acidified to pH 6.5 with (2N) hydrochloric acid and then to pH 7 with a sodium bicarbonate solution. This solution was filtered and added via syringe to (500 mg) evacuated maleimide loaded glass support. The reaction was shaken for 4 hours, filtered, washed with water, then ether, and dried in vacuo.

Chromatographic Standardization of 99m-MAG3:

Technetium labelled MAG3 and the weak complex $^{99m}$Tc-gluconate prepared by conventional solution techniques were standardized on three chromatographic systems for determination of the extent of the transchelation reaction on the solid support. $^{99m}$Tc-MAG3 was prepared by placing in a 1.5 mL tube 0.5 mg N-S-benzoyl-MAG3, 200 μL saline, 100 μL pertechnetate and 100 μL stannous gluconate (50 μg stannous chloride and 1 mg sodium gluconate). The tube was capped and placed in boiling water bath for 10 minutes. $^{99m}$Tc-gluconate was prepared from 200 μL saline, 100 L pertechnetate and 100 L stannous gluconate.

| | Migration of radioactive species | | | | | | |
|---|---|---|---|---|---|---|---|
| Whatman No. 1 strips/ | 1.05 | 0.91 | 0.09 | 0.03 | | | $^{99mTc}$-MAG3 |
| acetone | 1.31 | 0.01 | 0.00 | 0.01 | | | $^{99mTc}$-gluconate |
| Whatman No. Strips/ | 0.02 | 0.00 | 0.01 | 0.17 | 1.20 | 0.22 | $^{99mTc}$-MAG3 |
| acetonitrile:water 60:40 | 0.15 | 0.48 | 0.87 | 0.24 | 0.01 | 0.01 | $^{99mTc}$-gluconate |
| Gelman ITLC-SG strips/ | 0.01 | 0.01 | 0.01 | 3.21 | | | $^{99mTc}$-MAG3 |
| saline | 0.02 | 0.01 | 0.02 | 1.53 | | | $^{99mTc}$-gluconate |

Labelling MAG3 on Maleimide Support:

To 260 mg of MAG3 loaded controlled-pore-glass maleimide support prepared by method 2 and evacuated by water aspirator was added a mixture of 300 μL saline, 200 μL pertechnetate and 100 μL stannous gluconate. After 10 minutes vacuum was released to check for reaction progress at room temperature. Thin layer chromatography (Whatman No.1 paper strips/acetonitrile:water) indicated some formation of $^{99m}$Tc-MAG 3 but much $^{99m}$Tc-gluconate remained.

| | Migration of radioactive species | | | | | |
|---|---|---|---|---|---|---|
| Whatman No. 1 strips/ acetone | 0.78 | 0.00 | 0.00 | 0.01 | | |
| Whatman No. 1 strips/ acetonitrile:water 60:40 | 0.30 | 0.26 | 0.39 | 0.49 | 0.26 | 0.24 |
| Gelman ITLC-SG strips/ saline | 0.01 | 0.01 | 0.01 | 3.21 | | |

The reaction mixture was transferred to a 10 mL tube, capped, evacuated and placed in boiling water bath for 10 minutes to facilitate complex formation. Thin layer chromatography indicated complete transchelation of $^{99m}$Tc-gluconate to $^{99m}$Tc-MAG3.

| | Migration of radioactive species | | | | | |
|---|---|---|---|---|---|---|
| Whatman No. 1 strips/ acetone | 1.08 | 0.31 | 0.02 | 0.14 | | |
| Whatman No. 1 strips/ acetonitrile:water 60:40 | 0.00 | 0.00 | 0.15 | 0.55 | 0.74 | 0.46 |
| Gelman ITLC-SG strips/ saline | 0.00 | 0.00 | 0.00 | 1.63 | | |

EXAMPLE 3

Preparation of Maleimide Functionalized Agarose Support:

To 3 g of a swollen alkylamine functionalized cross-linked agarose support (Biorad Affi-Gel 102) at 0° C. was added a solution of 100 mg N-maleimidoethyl formate in 6 mL aqueous bicarbonate. After 30 min of occasional shaking the support was then shaken mechanically at room temperature for 1 hr. The support was filtered and washed 3 times with water and filtered again.

Loading MAG3 on Maleimide Functionalized Agarose Support:

To 1 g of maleimido functionalized support was added a solution of 15 mg MAG3 in 3 mL aqueous bicarbonate. The reaction was shaken at room temperature for 12 hours. The support was filtered and washed with water then filtered again to remove excess water from the swollen beads. Amino acid analysis showed 6.12 μmoles/g (dry).

Loading Ligand-Targeting Molecule Conjugate on Maleimide Functionalized Agarose Support:

To 1 g of maleimido functionalized support was added a solution of 25 mg of a ligand-peptide conjugate Pic-Ser-Cys-Gly-TKPPR (SEQ ID NO: 2) (Pic-Ser-Cys ligand; Gly-TKPPR targeting peptide) in 3 mL aqueous bicarbonate. The reaction was shaken at 0° C. for 30 minutes. The support was filtered and washed with water then filtered again to remove excess water from the swollen beads. Amino acid analysis showed 5.0 μmoles/g (swollen) or 99.5 μmoles/g (dry).

Labelling:

To (100 mg) of the loaded agarose support in a stoppered glass syringe vessel was added (10 mCi, 100 μL) sodium pertechnetate, (100 μL) saline, and (100 μL) stannous-gluconate solution. The vessel was shaken gently to mix then heated 10 minutes in a boiling water bath. Fractions of eluent were collected by adding portions of saline or ethanol to the top of the support followed by drawing the eluent into vacutainer vials via injection. The activity of each fraction was measured in a Capintec gamma counter. The first fraction was then analyzed by RP-HPLC to assess purity (labelled ligand vs labelled pertechnetate and other labelled impurities).

The MAG3 labelled product was 80.5% pure while the ligand-peptide conjugate Pic-Ser-Cys-Gly-TKPPR (SEQ ID NO: 2) labelled product was 86.3% pure.

EXAMPLE 4

Preparation of Maleimido Functionalized Silica:

To 1.0 g of evacuated 3-propylamine functionalized silica support (Aldrich 36,425-8) was added a solution of 50 mg N-maleimidoethyl formate in 4 mL aqueous bicarbonate at 0° C. After 45 minutes of occasional shaking, 16 mL water was added. The support was shaken mechanically at room temperature for 15 minutes and then filtered and washed with water.

Loading MAG3 on Maleimide Functionalized Silica Support:

To 1 g of maleimido functionalized silica sup port was added a solution of 20 mg MAG3 in 3 mL aqueous bicarbonate. The reaction was shaken in an ice water bath for 12 hours and then allowed to warm to room temperature. The support was filtered and washed with water then filtered again to remove excess water from the swollen beads. Amino acid analysis showed 78.4 μmoles/g (dry).

Labelling MAG3 on Maleimide Functionalized Silica Support:

To (100 mg) of the loaded support in a stoppered glass syringe vessel was added (10 mCi, 100 μL) sodium pertechnetate, (100 μL) saline, and (100 μL) stannous-gluconate solution. The vessel was shaken gently to mix then heated 10 minutes in a boiling water bath. Fractions of eluent were collected by adding portions of saline or ethanol to the top of the support followed by drawing the eluent into vacutainer vials. The activity of each fraction was measured in a Capintec gamma counter. The first fraction was then analyzed by RP-HPLC and assessed to be 97.1% pure (labelled MAG3 vs labelled pertechnetate and other labelled impurities).

EXAMPLE 5

Preparation of Maleimido Functionalized Acrylic Support:

To 1.5 g evacuated alkylamine functionalized acrylic support (Sigma) was added a solution of 10 mL aqueous bicarbonate at 0° C. followed by 155 mg, powdered N-maleimidoethyl formate. After 20 minutes of occasional shaking the support was then shaken mechanically at room temperature for 1.5 hours. The support was filtered and washed with water, then methanol and then filtered and dried in vacuo.

Loading MAG3 on Maleimide Functionalized Acrylic Support:

To 1 g of maleimido functionalized acrylic support was added a solution of 20 mg MAG3 in 3 mL aqueous bicarbonate, the reaction shaken at room temperature for 3 hours. The support was filtered and washed with water then filtered again to remove excess water from the swollen beads. Amino acid analysis showed 17.4 μmoles/g (dry).

Loading Ligand-Peptide Conjugate on Maleimide Functionalized Acrylic Support:

To 1 g of maleimido functionalized acrylic support was added a solution of 25 mg of the ligand-peptide conjugate Pic-Ser-Cys-Gly-TKPPR (SEQ ID NO: 2) in 3 mL aqueous bicarbonate. The reaction was shaken at room temperature for 4 hours. The support was filtered and washed with water then filtered again to remove excess water from the swollen beads. Amino acid analysis showed 29 μmoles/g (dry).

Labelling:

To (100 mg) of the loaded agarose support in a stoppered glass syringe vessel was added (10 mCi, 100 μL) sodium pertechnetate, (100 μL) saline, and (100 μL) stannous-gluconate solution. The vessel was shaken gently to mix then heated 10 minutes in a boiling water bath. Fractions of eluent were collected by adding portions of saline or ethanol to the top of the support followed by drawing the eluent into vacutainer vials via injection. The activity of each fraction was measured in a Capintec gamma counter. The first fraction was then analyzed by RP-HPLC to assess purity (labelled ligand vs labelled pertechnetate and other labelled impurities).

The MAG3 labelled product was 97% pure while the ligand-peptide conjugate Pic-Ser-Cys-Gly-TKPPR (SEQ ID NO: 2) labelled product was 85% pure.

EXAMPLE 6

Labelling Ligands on Maleimide Functionalized Controlled Pore Glass Support:

Maleimide functionalized controlled pore glass supports prepared in the manner described in example 2 were loaded with MAG3 and ligand-peptide conjugate Pic-Ser-Cys-Gly-TKPPR. The immobilized ligands were labelled according to the procedures described in examples 3 to 5. The activity of first fraction of the eluent was measured in a Capintec gamma counter and analyzed by RP-HPLC to assess purity. The MAG3 labelled product was 93% pure while the ligand-peptide conjugate Pic-Ser-Cys-Gly-TKPPR (SEQ ID NO. 2) was 59.7% pure.

I claim:

1. A composition useful for generating a metal labelled imaging agent, the composition comprising:
  a solid support; a linking group bound to the solid support; and a conjugate comprising a ligand and a targeting molecule wherein the ligand incorporates a metal coordinating atom that is coupled to the linking group by a bond cleavable by said metal.

2. A composition according to claim 1, wherein said ligand is a peptide.

3. A composition according to claim 1, wherein said targeting molecule is a peptide.

4. A composition according to claim 1, wherein said conjugate is a peptide.

5. A composition according to claim 2, wherein said targeting molecule comprises the sequence Thr-Lys-Pro-Pro-Arg (SEQ ID NO: 1).

6. A composition according to claim 4 wherein the conjugate is a peptide selected from Pic-Ser-Cys-Gly-Thr-Lys-Pro-Pro-Arg (SEQ ID NO: 2) and N, N'-dimethyl-Gly-Ser-Cys-Gly-Thr-Lys-Pro-Pro-Arg (SEQ ID NO: 3).

7. A composition according to claim 1, wherein the metal coordinating atom is a sulfur atom-incorporated in a cysteine residue of the ligand.

8. A composition according to claim 1, wherein the metal is $^{99m}$Tc.

9. A composition according to claim 1, wherein the solid support is selected from controlled-pore glass, acrylic, silica and agarose.

10. A composition according to claim 1, wherein the linking group is selected from dihydropyran and maleimide.

11. A process for generating a metal labelled imaging agent, comprising the steps of:
  (1) obtaining a composition according to claim 1;
  (2) contacting the composition with said metal to cause the formation of a coordinate bond between the metal and the metal coordinating atom of the ligand and thereby the release of a metal labelled conjugate from the support; and
  (3) collecting the metal labelled conjugate so released.

12. A process according to claim 11, wherein said metal is $^{99m}$Tc.

13. A composition useful for generating a metal labelled imaging agent, the composition comprising: a solid support; a maleimide linking group bound to the solid support; and a ligand incorporating at least one metal coordinating sulfur atom that is coupled to the linking group by a bond cleavable by said metal.

14. A composition according to claim 13, wherein said metal is $^{99m}$Tc.

15. A composition according to claim 14, wherein said solid support is selected from controlled-pore glass, silica, acrylic and agarose.

16. A composition according to claim 14, wherein said ligand is a peptide or derivative thereof.

17. A composition according to claim 16, wherein said ligand is mercaptoacetyl-glycyl-glycyl-glycine.

18. A composition according to claim 16, wherein said ligand is coupled to a targeting molecule thereby forming a conjugate.

19. A composition according to claim 18, wherein said conjugate is selected from Pic-Ser-Cys-Gly-Thr-Lys-Pro-Pro-Arg (SEQ ID NO: 2) and N,N'-dimethyl-Gly-Ser-Cys-Gly-Thr-Lys-Pro-Pro-Arg (SEQ ID NO: 3).

20. A process for generating a metal labelled imaging agent, comprising the steps of
  (1) obtaining a composition according to claim 13;
  (2) contacting the composition with said metal to cause the formation of a coordinate bond between the metal and metal coordinating sulfur atom and the release of a metal labelled ligand from the support; and
  (3) collecting the metal labelled ligand so released.

21. A process according to claim 20, wherein said metal is $^{99m}$Tc.

22. A process according to claim 20, further comprising the step of coupling the metal labelled ligand with a targeting molecule.

* * * * *

UNITED STATES PATENT AND TRADEMARK OFFICE
CERTIFICATE OF CORRECTION

PATENT NO. : 5,789,555
DATED : August 4, 1998
INVENTOR(S) : Pollak et al.

It is certified that error appears in the above-identified patent and that said Letters Patent is hereby corrected as shown below:

On the title page, item [73], delete "Robert Dunn-Default" insert - therefor -- Robert Dunn - Dufault --

Signed and Sealed this

Twenty-ninth Day of June, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 1:

Thr Lys Pro Pro Arg
1               5

( 2 ) INFORMATION FOR SEQ ID NO: 2:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: misc_feature ( B ) LOCATION: 1
            ( D ) OTHER INFORMATION: /note= "Picolinic acid is attached to
                Ser of position 1."

( x i ) SEQUENCE DESCRIPTION: SEQ ID NO: 2:

Ser  Cys  Gly  Thr  Lys  Pro  Pro  Arg
    1                 5

( 2 ) INFORMATION FOR SEQ ID NO: 3:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: misc_feature
            ( B ) LOCATION: 1
            ( D ) OTHER INFORMATION: /note= "N,N'-dimethyl is attached to
                Gly of position 1."

( x i ) SEQUENCE DESCRIPTION: SEQ ID NO: 3:

Gly  Ser  Cys  Gly  Thr  Lys  Pro  Pro  Arg
    1                 5